United States Patent [19]

Sung et al.

[11] 4,129,944

[45] Dec. 19, 1978

[54] DENTAL CONSTRUCTIONS AND DENTAL ALLOYS

[75] Inventors: Pei Sung, Lawrenceville; Irving Klaus, Highland Park Borough; James Lee-You, Cranbury, all of N.J.

[73] Assignee: Johnson & Johnson, New Brunswick, N.Y.

[21] Appl. No.: 771,507

[22] Filed: Feb. 24, 1977

Related U.S. Application Data

[63] Continuation-in-part of Ser. No. 546,642, Feb. 3, 1975, abandoned, which is a continuation-in-part of Ser. No. 376,767, Jul. 5, 1973, abandoned.

[51] Int. Cl.² ............................................. A61C 13/00
[52] U.S. Cl. .......................................................... 32/8
[58] Field of Search ............................ 32/8, 2; 75/171

[56] References Cited

U.S. PATENT DOCUMENTS

| | | | |
|---|---|---|---|
| 2,190,840 | 2/1940 | Kay | 75/171 |
| 2,864,696 | 12/1958 | Foreman | 75/171 |
| 2,897,595 | 8/1959 | Lee | 32/8 |
| 2,936,229 | 5/1960 | Shepard | 75/171 |
| 3,834,024 | 9/1974 | Kochavi | 32/8 |
| 3,896,547 | 7/1975 | Kulwiec | 32/10 |

*Primary Examiner*—Robert Peshock

[57] ABSTRACT

The invention relates to dental constructions such as bridges, crowns and the like comprising a metal core and porcelain or other tooth simulating material bonded thereto, and to dental alloys having good physical strength, corrosion resistance, workability and ability to bond to porcelain. The dental alloys have a base cost of substantially less than gold but are equal to or better than gold for many dental applications. The alloys are also useful in dental applications not requiring bonding to porcelain or plastic as in the preparation of metal inlays or onlays.

The metal cores of the dental construction are alloys composed primarily of nickel, chromium and silicon and containing on a weight percent basis, about 65 to 75 percent nickel, about 15 to 23.5 percent chromium and about 3.5 to 6 percent silicon, to which a small amount of molybdenum and boron are added. The molybdenum is present within the range of 3 to 5 percent and boron within the range of 0.2 to 2 percent by weight of the total alloy composition. The alloys have excellent physical properties for dental applications having a fusion temperature with the range of about 2050° to 2350° F., a coefficient of expansion of from about $13.0 \times 10^{-6}$ in/in/° C. to about $13.8 \times 10^{-6}$ in/in/° C., good corrosion resistance when compared with similarly cast gold or other commercial nonprecious metal dental alloys and good oxidation resistance. They also have as casted, a tensile strength of at least 90,000 psi, an elongation of about 0.5 to 5.0 percent, a Rockwell C hardness within the range of about 25 to 33, and good bonding to porcelain.

6 Claims, No Drawings

DENTAL CONSTRUCTIONS AND DENTAL ALLOYS

BACKGROUND OF THE INVENTION

The present invention relates to dental constructions and to dental alloy compositions. This application is a continuation-in-part of our copending application Ser. No. 546,642, filed Feb. 3, 1975 which was a continuation-in-part of application Ser. No. 376,767, filed July 5, 1973, both applications now abandoned.

Dental restorations such as bridges, crown, dentures, partial dentures, inlays, onlays and the like have employed gold alloy for many years. Because of its high cost, many attempts have been made to make and employ non-precious metal alloys in place of the gold. Such non-precious metal alloy compositions are illustrated, for example, by the patents, U.S. Pat. Nos. 1,736,053; 2,089,587; 2,156,757, 2,134,423; 2,162,252; 2,631,095; 3,131,629; 3,464,817 and 3,544,315. Also in the November 3, 1970, issue of the *British Dental Journal* there is an article appearing at pages 419 to 423 entitled "The Properties of Nickel-Chromium Casting Alloys Containing Boron and Silicon" authored by H. J. Harcourt, M. Riddihough and John Osborne. This article reports on various nickel-chromium-boron-silicon aloys and their properties and suitability for dental uses.

Gold alloys, however, have many advantageous properties as a dental alloy and many of the previously prepared non-precious metal alloys have been found to be unsatisfactory in various respects when compared to the conventional gold alloy.

One of the problems encountered in attempts to use non-precious metal alloys for dental work in place of gold is that many of these alloys have been hard to cast because of a high melting range. In order to be accepted generally by dental laboratory technicians, the melting temperature of the alloy should not be much in excess of 2400° F. It is desirably within the range of about 2000° to 2350° F., more preferably, nearer the lower limits. A practical reason for this is that many dental laboratories use torches of the gas oxygen type which will not heat to much about 2500° F. so that if higher melting alloys are used then special heating equipment such as oxygen-acetylene torches must be obtained for working the metal. Although attempts have been made to adapt these alloys by modifying casting techniques such as by using special investment materials, etc.

Another problem with many of the heretofore known non-precious metal dental alloys is one of corrosion. Not only does corrosion cause loss of restorations such as porcelain jackets, crowns, bridges, etc., which are faced with porcelain, corrosion may cause, in the case of certain non-precious metal alloys formation of colored ions which discolor the porcelain.

A still further serious problem encountered in constructing a metal core or framework is the difficulty of soldering the non-precious metal alloy parts to themselves or to gold by using the conventional dental solders.

In addition, the coefficient of expansion must be compatible with porcelain. Where there is not the desired compatibility in the coefficient of expansion between the metal and porcelain, fractures may develop in the porcelain during the firing and subsequent cooling. The preferred relationship of porcelain to metal is such that at room temperature there is compression in the porcelain or glass layer and tension in the metal. Further, the fusion temperature of the alloy, while it should not be so high as to be difficult to cast, it must be sufficiently above the firing temperature of the porcelain so that there is no deformation of the metallic core during firing. Moreover, metal alloys must bond adequately to porcelain so that when subjected to mechanical stress, there does not occur a separation at the interface in whole or in part.

Thus, it is the object of the present invention to provide for a dental construction such as bridges, crowns, etc., having a metal core of a non-precious metal alloy and a tooth enamel simulating outer covering bonded thereto wherein said non-precious metal alloy is free from the objections enumerated above and moreover the relationship of the physical properties between the metal core and outer covering are such that the foregoing problems are met. The preparation of a non-precious metal dental alloy which is particularly suitable in dental constructions but which may be employed in other dental applications is another object of the present invention. Another object is to provide for a dental construction which employs a non-precious metal alloy which is not only less costly than gold but has advantages over gold as dental structural material. A further object is the provision of a dental alloy which may be employed without appreciably changing present techniques or equipment.

BRIEF DESCRIPTION OF THE INVENTION

It has now been discovered that a dental construction comprising an appropriately contoured metal core of a non-precious metal alloy with a porcelain covering bonded thereto may be prepared which accomplishes the objects hereinbefore enumerated by employing for the metal core, a metal alloy having a fusion temperature within the range of from 2050° F. to 2350° F. and a coefficient of expansion in the range of from about $13.0 \times 10^{-6}$ in/in/° C. to about $13.8 \times 10^{-6}$ in/in/° C.

The expression "dental construction" as herein employed is meant a metal core of a non-precious metal alloy contoured in a desired form and at least one layer of porcelain bonded thereto. "Porcelain" as herein employed is meant dental porcelain as is known in the art and which is subsequently more fully described and illustrated. Normally in dental restoration porcelain is applied in several coatings and firings. Under present practice the porcelain which is bonded to metal is that understood in the art as opaque porcelain, as subsequently illustrated, but the present invention is not limited thereto. The expression "core" as herein employed is the metal framework or base, at least a portion of which is to be covered with porcelain. It may have any shape, depending on the dental restoration intended. The "coefficient of expansion" for the metal alloy as herein employed is the linear thermal expansion coefficient determined in the usual manner from values obtained on heating from room temperature up to 600° C. at a rate of 5°/minute.

The metal alloys in such core and which of themselves constitute a part of the invention, are prepared from nickel, chromium, and silicon together with other elements in the proportions and manner thereinafter more fully described. The preferred alloys for use as structural metals for the preparation of bridges, crowns, copings etc., or for use in inlays and onlays contain in addition to the nickel, chromium and silicon, small amounts of molybdenum together with boron. The alloys of the present invention contain about 65 to 75 percent nickel, about 15 to 23.5 percent, preferably 15 to 21 percent chromium and about 3.5 to 6 percent silicon, together with 3 to 5 percent molybdenum and 0.2 to 2 percent boron. The properties of the alloys, in addition to the fusion temperature and coefficient of expansion above recited, are good corrosion resistance, good oxidation resistance, a tensile strength of at least 90,000 psi, a percent elongation of about 0.5 to 5.0, a Rockwell C hardness within the range of about 25 to 33. The alloys bond well to porcelain and shear strengths at the interface designated as porcelain bonding strength may be obtained which are greater than 7300 psi.

These properties are particularly advantageous for the preparation of the dental constructions and further in imparting desirable properties to the dental constructions made therefrom as hereinafter more fully described.

DETAILED DESCRIPTION OF THE INVENTION

The dental construction of the present invention comprises an appropriately contoured core of a novel non-precious metal alloy with a porcelain covering bonded thereto. The novel metal alloys which are an aspect of the present invention have a fusion temperature within the range of 2050° to 2350° F. and a coefficient of expansion in the range of from about $13.0 \times 10^{-6}$ in/in/° C. to about $13.8 \times 10^{-6}$ in/in/° C. and consists essentially of nickel, chromium and silicon, and have added thereto minor amounts of molybdenum and boron.

The composition of the novel alloys are from about 65 to 75 percent nickel, about 15 to 23.5 percent, preferably 15-21 percent chromium, about 3.5 to 6 percent silicon, about 3 to 5 percent molybdenum and about 0.2 to 2 percent boron. Manganese in amounts up to 1 percent may be substituted for boron in some compositions but is less preferred. In the specification and claims, the percentages are on a weight basis.

These alloys have properties suitable for use as a structural metal in dental constructions, where they are to be faced with a tooth enamel simulating material and a dental construction of the instant alloy faced with a tooth enamel simulating material, especially when such material is a porcelain, constitutes a part of the present invention. They may also be faced with plastics such as acrylics and further are useful as a dental metal without a facing. Those with boron content at the lower range are also useful for inlays, onlays and partial dentures. In addition to the above-cited fusion temperatures and coefficient of expansion, other properties exhibited by the alloy include good corrosion resistance, good oxidation resistance, an ultimate tensile strength in the range of 90,000 to 140,000 psi, a percent elongation of about 0.5 to 5.0, a Rockwell C hardness within the range of about 25 to 33.

Within the scope of suitable alloys, a preferred composition is that consisting essentially of in percent by weight: about 69 to 72 percent of nickel, about 18 to 20 percent chromium, about 4 to 5.5 percent silicon, about 4 to 4.5 percent molybdenum and about 1 to 1.5 percent boron. The fusion temperature of the alloys of the preferred composition is in the range of about 2050° to 2165° F.

The fusion temperature range of 2050°-2350° F. of the alloys are within the range in which the dental laboratories are usually accustomed to work so that the alloy may be cast for the preparation of metal cores and other structural materials without change in equipment and technique. Moreover, the fusion temperature is sufficiently high so that when the metal core is to be faced with porcelain it can resist deformation during the firing steps in porcelainization. Thus, the fusion properties of the alloys are ideally suited for dental construction to be faced with a tooth-simulating porcelain covering.

The coefficient of expansion in the range of $13.0 \times 10^{-6}$ in/in/° C. to about $13.8 \times 10^{-6}$ in/in/° C. is suited to be employed with many dental porcelains. When suitable porcelains as subsequently more fully described are applied to the surfaces of the novel alloys, they are resistant to checking and other fractures which have tended to occur during the process of heating to the firing temperature followed by cooling to room temperature. Further, when employed with porcelain with expansion and contraction characteristics such that after cooling, the porcelain is under compression at room temperature, especially good results are obtained. Moreover, when bonded to porcelain, a good porcelain to metal bond is formed. The shear strengths at the interface designated as the porcelain bonding strength may be obtained which are greater than 7300 psi.

In addition to the foregoing, another property important in its function as a metal core which is to be faced with porcelain is the absence of metals which form colored metal ions. Many metal alloys which may be desirable from strenghth and other properties frequently contain cobalt, copper or iron and are therefore unsuitable for metal structure which is to be faced with porcelain. The present alloys possess desirable properties without inclusion of such metals and a metal core of the present alloys may be faced with porcelain or plastic without staining.

In addition to the foregoing, other properties of the alloys render them superior as dental structural materials whether or not they are to be faced with porcelain. The alloys have good strength, hardness, corrosion resistance and oxidation resistance while being lighter, stronger and harder than gold. It is recognized that the term good is relative, but as used herein it means good for the purposes of use in dentistry for which the material is specified. Thus, good strength and hardness as herein employed would be tensile strength and hardness above that of the presently available gold alloys. Good corrosion resistance would be resistance to etching by hydrochloric acid and lactic acid superior to that shown by presently commercially available non-precious metal dental alloys and resistance to etching by aqueous sodium chloride solution comparable to that shown by conventionally used dental alloys. Good oxidation resistance would be such that the surface of the metal would not oxidize during working to the degree that bonding to porcelain is made difficult.

The ultimate tensile strength of about 90,000 to 140,000 p.s.i., compare favorably with that of about 65,000 p.s.i. to 70,000 p.s.i. for gold. The hardness of below about 35 Rockwell C (below about 120 Rockwell B) compares favorably with the about 86 Rockwell B hardness for gold. Thus, the alloys have strength and hardness superior to gold while not being so hard as to prevent grinding and polishing of dental structures to the desired shape and smoothness. (The Rockwell C hardness values of the present alloys may be converted to Rockwell B hardness for purposes of comparison with gold using standard tables and calculations.)

The good corrosion resistance exhibited by the alloys of the present invention may be seen by the minor extent of etching as measured by weight loss after immersion at room temperature, for 20 days in 0.05% hydrochloric acid, 0.1% lactic acid or 1% sodium chloride solution. The extent of etching on immersion in such hydrochloric acid solution is in the range of 0.1 to 0.2 milligram per square centimeter per day (mg/cm$^2$/day) and in such lactic acid solution is in the range of 0.01 to 0.03 mg/cm$^2$/day, significantly less than that of presently available non-precious metal alloys. The extent of etching in a 1% sodium chloride solution is in the range of about 0.0015 to 0.009 mg/cm$^2$/day, comparable to and even superior to the 0.002 to 0.01 mg/cm$^2$/day of conventional dental gold alloys.

The good oxidation resistance exhibited by the alloys of the present invention may be seen by the minor extent of oxide formation as measured by weight gain on heating at 1800° F. for five minutes. The extent of oxidation under such conditions is generally no greater than about $0.7 \times 10^{-2}$ mg/cm$^2$ - min, an amount insufficient to interfere with or make difficult the operation of bonding to porcelain.

In addition to the foregoing, the alloy can be remelted and cast without loss of their excellent physical properties, it may be used with the dental solders presently employed when working with gold or with non-precious metal alloy solders, and may be faced with dental plastic materials such as the acrylics.

In the alloy compositions of the present invention, not only is the actual amount of the metal component important but also the relationship of certain components to each other. One important relationship is that of chromium to nickel. When the chromium content with respect to the nickel is permitted to become too high, the thermal expansion of the alloy is found to be too low to obtain good matching with porcelain. Where the chromium content becomes too low, the alloy is generally found to have substantially poorer oxidation and corrosion resistance than desirable. A chromium to nickel ratio of about 0.24 to 0.30 has been found to impart desirable properties to the alloy. A preferred ratio range is from 0.26 to 0.27. These ratios are to be considered together with the total nickel in the alloys.

As previously indicated, the silicon is preferably present in the range of about 4 to 5.5% by weight. Where used in amounts much below 4%, the fusion temperature of the alloy is found to be high.

When the silicon content is increased to much above 6.0% the alloy tends to become brittle and lose some of its mechanical strength. For the purposes intended it is critical and essential that the silicon content of the alloy not exceed about 6%.

The addition of molybdenum to the nickel, chromium and silicon stabilizes the thermal expansion property of the alloy against change which tends to occur during the repeated firing which are necessary procedures when porcelain is fused to the structural metal during the preparation of jackets, crowns, bridges and the like. Further, molybdenum has the property of improving corrosion resistance.

Inclusion of the boron or manganese improves the bonding strength between the alloy and porcelain. However, addition of manganese tends to decrease corrosion resistance and tends to discolor the porcelain. Hence, the preferred alloy compositions contemplate the use of boron. However, it is critical and essential that boron not be employed in excess of about 2% by weight since boron tends to increase brittleness.

In addition to the criticality of the maximum amount of boron which should be added, there is a critical relationship between the relative amounts of silicon and boron. Thus, when the amount of boron is increased, the amount of silicon is decreased. Within the limits of the amount of silicon and amount of boron which may be present in the alloy composition.

The dental alloy composition intended for use as structural metal may contain minor amounts of other materials which may be present as impurities in the metals employed to prepare the alloy. None of these are essential in the dental alloy compositions of the present invention. Accordingly, the alloy compositions of the present invention consist essentially of nickel, chromium and silicon with molybdenum and boron or less preferably with manganese replacing a portion of the boron.

The alloy may be prepared in a conventional manner such as by placing the components in a fused alumina crucible and fusing the ingredients with appropriate mixing. While in the molten state, the alloy may be poured into molds for ingot formation.

The dental alloys of the present invention intended for use as structural metals may be employed in the replacement of the heavier and more expensive gold which has been the conventional structural metal used for dental purposes. The alloys are ideally suited for use where bonding of the alloy to a porcelain is required, as in the preparation of artificial teeth, crowns, bridges and the like. The alloy may also be used in the preparation of veneers, both plastic as well as porcelain. Their physical properties also make the alloys highly useful for the preparation of metal crowns where the metal acts to completely cover the prepared tooth and for the preparation of inlays and onlays. In such usage the dental alloys of the present invention are found to be not only as good as the gold which has heretofore been used but in many respects superior to such gold.

The dental constructions of the present invention may be obtained by first preparing an appropriately contoured metal core made of the novel metal alloy of the present invention by casting according to conventional procedures and thereafter painting the metal core with porcelain and firing to secure the porcelain on the metal by bonding. Thereafter, additional layers of porcelain are applied with firing after each step to obtain an artificial tooth or other dental restoration.

By "porcelain" is meant dental porcelain as is known in the art and embraces dental glasses. They generally contain silicon oxide, aluminum oxide, sodium oxide, potassium oxides and minor amounts of other oxides. Normally, the porcelain covering which is first applied to the metal is an opaque porcelain. An opaque porcelain reduces the tendency of the metal to be seen through the final coating. Opaque porcelains are available commercially and include in the oxide composition either zicronium oxide, tin oxide, zinc oxide, titanium oxide or zirconium silicate as an opaquing agent. The opaque porcelain is normally coated with additional layers of body porcelain followed by a layer of incisal porcelain under conventional procedures. The body porcelain is available commercially as gingival porcelain and may have a small amount of opaquing agent and incisal porcelain has no opaquing agent.

The exact composition of the porcelains is not critical although generally speaking, the porcelains are to be selected from those employing orthoclase feldspar as raw material. It is essential however that certain properties be observed in the selection of an appropriate porcelain. Thus, the porcelains should have a fusion temperature maximum of about 1850° F. and coefficient of thermal expansion in the range of about $10 \times 10^{-6}$ in/in/° C. to about $21 \times 10^{-6}$ in/in/° C. It is recognized that a meaningful single coefficient of expansion is not obtainable for porcelain as it is for metal over the broad temperature range of from about room temperature up to 600° C. and that coefficients of expansion values are valid only for a narrower range of temperatures. Porcelains which may be employed with the metal alloy of the present invention will be those whose several coefficients of expansion are within the above ranges when determined at several temperature ranges up to about 575°-600° C.

Typical porcelain compositions are found in standard references such as Skinner and Phillips, "The Science of Dental Materials," p. 518, W. B. Saunders Company, Philadelphia and London 1967; the compositions of several commercial porcelains are listed on page 60 of Jean-Marc Meyer, "Contributions à l'Étude de la Liaison Céramometallique des Porcelaines cuites sur Alliages en Prosthèse Dentaire", Thesis, University of Geneva, 1971. Suitable porcelains include those having compositions described in U.S. Pat. No. 3,052,982 of the following oxide content: 61–67.8% $SiO_2$; 11.7–17.1% $Al_2O_3$; 0.1–2.6% CaO; 0.1–1.8% MgO; 2.37–9.6% $Na_2O$ and 6.7–19.3% $K_2O$. The foregoing composition may be modified to include lithium oxide in amounts up to 5% and the other oxides reduced or modified. In addition, the porcelain may be modified to add from about 0.05 to about 25% of an opaquing agent and the other oxides reduced or modified as desired limited by the need to keep the temperature and expansion properties within the desired limits. Suitable opaque porcelains may have the oxides in the following approximate ranges: $SiO_2$ 47 to 63%; $Al_2O_3$ 10 to 14%; CaO 0.6 to 1.3%; $K_2O$ 8.5 to 11%; $Na_2O$ 1.5 to 5%; MgO 0.4 to 0.8%; and $SnO_2$ 9 to 25%. The present invention is not directed to the chemical composition of the porcelain, thus, any commercially available dental porcelain or porcelain compositions prepared by a skilled artisan may be employed in the dental construction provided the foregoing properties are met.

From the porcelains of the type described above, particular porcelains may be selected for bonding to the alloys of the present invention to obtain good bonding properties by empirical tests. One such test employs rods of alloy and porcelain of the same dimensions, preferably thin rods about 2 inches in length. The rods are heated from room temperature up to about 600° C. and the lengths measured at 575° C. Those porcelain rods whose lengths are within about 6% of the length of the alloy rods are considered to be a good match for purposes of providing a covering for the alloy with good bonding properties.

In carrying out the preparation of the dental construction of the present invention from the novel alloy of the present invention, the metal core is formed by casting into casting investments which have previously been prepared by conventional procedures. Pellets or slugs of the metal alloy of the present invention are placed in a hot crucible, heated in a conventional manner until the alloy melts. The alloy melt is cast employing conventional procedures and apparatus such as a centrifugal casting machine to obtain a casting contoured roughly to the shape desired for the core. The casting is recovered employing conventional procedures, cleaned and then ground to the desired final shape, washed and dried.

After the grinding step, the areas of the metal core which is to receive porcelain is sandblasted with a quartz abrasive and the shoulders which are not to receive the porcelain are polished. The cores then are placed in hydrofluoric acid for a short time (preferably about 5 minutes), then rinsed in distilled water and thereafter cleaned, preferably ultrasonically in distilled water, and dried. The core units are then ready to receive the porcelain.

Porcelain, preferably opaque porcelain such as of the composition previously described, is applied to the sandblasted area of the metal core. The thus painted core or core units are (a) air dried, (b) placed into a furnace preheated to 1200° F. and (c) fired first under vacuum (26–29 inches of mercury) by raising the temperature up to about 1700° F. at a rate of about 90°–100° F./minute and then in air by breaking the vacuum and continuing the heating to about 1840°–1850° F. to obtain a dental construction comprising an appropriately contoured metal core having porcelain covering bonded thereto which is then removed from the furnace and cooled at ambient temperature.

Although good bonding is obtained between the metal alloy of the instant invention and porcelain having a coefficient of expansion hereinbefore specified, a superior chemical bond which imparts to the dental construction an even greater resistance to separation on stress may be provided by employing a bonding agent. The exact nature of the bonding agent is not critical. Any suitable bonding agent may be employed.

When a bonding agent is employed, the procedural steps after the grinding of the casting is modified and may be carried out as described hereinafter and more fully in the above-identified application. The ground core is cleaned ultrasonically with distilled water and dried. The bonding agent is then applied to that portion of the metal core which is to be coated with porcelain. The bonding agent is allowed to dry in the vestibule of the furnace. Then the treated metal core is placed in a furnace preheated to 1200° F. and thereafter raising the temperature of the furnace to 1850° F. in air. The core is then removed from the furnace and allowed to cool at ambient temperature. After cooling, the excess bonding agent is mechanically removed, and the core thereafter cleaned and dried to obtain a dental construction comprising an appropriately contoured metal core and a porcelain covering bonded thereto. Other suitable methods appropriate for the bonding agent chosen may also be employed.

Generally, additional layers of porcelains are fired onto the foregoing dental construction to obtain dental construction which is an aesthetically pleasing artificial tooth or other dental restoration. The additional layers of porcelains are provided by a gingival porcelain which forms the principal bulk of the body of the artificial tooth and an incisal porcelain which provides translucency to the outer tips. In carrying out the preparation of a dental construction which is an aesthetically pleasing dental restoration, several layers of gingival porcelain and thereafter layers of incisal porcelain are applied on the dental construction having a covering of opaque porcelain bonded thereto and fired by heating from 1200° F. to 1700° F. under vacuum (26–29 inches Hg) and further to 1800° F. in air, and then cooling at room temperature, in separate sequential operations. More than one firing may be necessary. The dental construction thus obtained is useful in dental prosthesis.

The following examples illustrate the invention but are not to be construed as limiting:

EXAMPLE 1

Into a fused alumina crucible, is added 1.4 grams of boron powder, 4.1 grams of particulated silicon in the form of small blocks, 4.2 grams of molybdenum and 19.0 grams of chromium in plate form. There is then added 71.3 grams of nickel shot. The crucible is then heated by induction heat in an argon atmosphere to prevent oxidation. The contents are brought to a temperature of about 1600° C. The melt is then permitted to cool to about 500° C. at which time the solid alloy is removed.

Test bars of this alloy are cast and are found to have an Ultimate Tensile Strength of 132,000 pounds per square inch, a Yielding Strength of 110,000 pounds per square inch, a Modulus of Elasticity of $25 \times 10^6$ pounds per square inch, a Percent Elongation of 1.45% and a Rockwell B hardness of 106 $R_B$. The alloy also has a Thermal Expansion Coefficient of $13.0 \times 10^{-6}$ in/in/° C., a melting temperature within the range of 2250° to 2300° F., and a casting temperature of 2400° F.

Portions of the alloy prepared in the above manner are tested for its casting characteristics using standard Lost Wax Technique casting procedures. The alloy is found to cast well.

Using standard techniques, portions of the alloy are used in the preparation of metal crowns and bridges; and porcelain bonded crowns and bridges where the porcelain is fused to the metal. No discoloration of porcelain is observed and good bonding is obtained.

The alloy may also be used for plastic coated crowns and bridges using the conventional techniques employed in making the same.

When working the alloy, it is preferred to use an oxygen-gas flame for melting rather than an oxygenacetylene flame although the latter can be employed if care is taken.

EXAMPLE 2

Employing the same technique as described in Example 1, a dental alloy is prepared having the composition in, percent by weight, of:

| Nickel | 67.8% |
| Chromium | 22.0% |
| Molybdenum | 4.2% |
| Silicon | 5.0% |
| Manganese | 1.0% |

This alloy has an Ultimate Tensile Strength of 118,500 pounds per square inch, a Yielding Strength of 85,000 pounds per square inch, a Modulus of Elasticity of $24 \times 10^6$ pounds per square inch, a percentage of Elongation of 3.5% and a Rockwell B hardness of 98 $R_B$.

The alloy is also found to cast well using the Lost Wax Technique and found to handle well in the preparation of metal crowns and bridges, porcelain bonded crowns and bridges, the preparation of inlays and onlays, and in the preparation of plastic bonded crowns and bridges. No staining is noted of the porcelain where porcelain and metal bonds are made. Also, excellent bond strengths are obtained.

EXAMPLE 3

The following Tables I and II set forth data comparing the corrosion resistance and oxidation resistance of alloys of Examples 1 and 2 with the corrosion resistance and oxidation resistance of representative presently commercially available materials. In order that uniform comparative results be obtained, all samples used in the oxidation and corrosion tests are prepared in the same manner. The samples are heated to their casting temperatures and then cast in air in accordance with standard Lost Wax Technique. The castings after cooling to room temperature are ground with grinding papers to 600 grits, then polished with cotton using 0.3 um alumina polishing powders.

For testing for corrosion resistance, Table I, the polished samples are washed in water, followed by washing in acetone. The samples are then heated in air to 1,000° F. and then placed in a desiccator to cool. The samples are then weighed, and the weight recorded. The samples are then placed in aqueous solutions of the concentration indicated and remain immersed in such solution at ambient temperature for 20 days. The samples are then dried, weighed, and the loss in weight calculated.

In Table I, Corrosion Resistance, values are given also for human tooth enamel, dental amalgam, and a copper zinc dental alloy. These values are those published by Kazuo Nagai in the Journal of Nihon University School of Dentistry, Tokyo, Japan, Volume 11, No. 4 Issue, 1969. Mr. Nagai in describing his method of sample preparation stated that the samples were cast and then polished in accordance with the manufacturer's instructions.

For testing oxidation resistance, Table II, the polished samples are then washed in water followed by washing in acetone. The same are then heated in air to 1,000° F., and then placed in a desiccator. On cooling the samples are weighed and weight recorded. The samples are then placed in a small furnace, $3 \times 3 \times 1\frac{1}{2}$ inches and heated at a temperature of 1800° F., for five minutes. The furnace is equated to the 1800° F. temperature before insertion of samples. After the five minute heating, the samples are removed and again placed in a desiccator and cooled. The samples are then weighed and the weight recorded with the difference in weight indicating the degree of oxidation.

TABLE I - EXAMPLE 3

| | COMPARISON OF CORROSION RESISTANCE IN AQUEOUS SOLUTIONS OF HYDROCHLORIC ACID, LACTIC ACID, AND SODIUM CHLORIDE | | | | | | | |
|---|---|---|---|---|---|---|---|---|
| | WEIGHT LOSS* | | | | | | | |
| | CERAMCO Non-Precious Alloy Example 1 | CERAMCO Non-Precious Alloy Example 2 | ULTRATEK[1] Non-Precious Alloy | CERAMCO BAK-ON[2] Yellow Gold | CERAMCO BAK-ON[2] White Gold | Human[3] Enamel | Almagam[3] | Cu-Zn[3] Alloy |
| 0.05% HCl | 0.111 | 0.184 | 0.203 | 0.0188 | 0.0211 | 40.60 | 0.94 | 1.01 |
| 1% Lactic Acid | | | | | | | | |
| 1% NaCl | 0.0239 | 0.0166 | 0.0164 | 0.0183 | 0.0269 | 94.20 | 0.83 | 0.68 |

TABLE I - EXAMPLE 3-continued
COMPARISON OF CORROSION RESISTANCE IN AQUEOUS SOLUTIONS OF HYDROCHLORIC ACID, LACTIC ACID, AND SODIUM CHLORIDE

| | WEIGHT LOSS* | | | | | | | |
|---|---|---|---|---|---|---|---|---|
| | CERAMCO Non-Precious Alloy Example 1 | CERAMCO Non-Precious Alloy Example 2 | ULTRATEK[1] Non-Precious Alloy | CERAMCO BAK-ON[2] Yellow Gold | CERAMCO BAK-ON[2] White Gold | Human[3] Enamel | Almagam[3] | Cu-Zn[3] Alloy |
| Solution | 0.0080 | 0.0020 | 0.0568 | 0.0104 | 0.0029 | — | 0.39 | 0.073 |

[1]ULTRATEK Product of AMERICAN PRECISION METALS, 1777 Murchison Drive, Burlingame, California 94010
[2]BAK-ON Trademark of Johnson & Johnson doing business through its wholly owned subsidiary, CERAMCO, INC. 31-16 Hunters Point Ave., Long Island City, N.Y.
[3]Obtained from Kazuo Nagai, Journal of Nihon University, School of Dentistry, Tokyo, Japan, Vol. 11, No. 4 Issue. 1969.
*The weight loss is given in milligrams per square centimeter per day after having been immersed in the indicated solution for a period of 20 days at ambient temperature in the laboratory.

TABLE II-EXAMPLE 3

| | OXIDATION RESISTANCE GIVEN IN MILLIGRAM PER SQUARE CENTIMETER PER MINUTES | | | | |
|---|---|---|---|---|---|
| | CERAMCO Non-Precious Alloy #1 | CERAMCO Non-Precious Alloy #2 | ULTRATEK Non-Precious Alloy | CERAMCO BAK-ON Yellow Gold | CERAMCO BAK-ON White Gold |
| Weight Gain per Unit Area and time (Mg/cm$^2$-min). | $0.4765 \times 10^{-2}$ | $0.6367 \times 10^{-2}$ | $0.7210 \times 10^{-2}$ | $0.2885 \times 10^{-2}$ | $0.3551 \times 10^{-2}$ |

EXAMPLE 4

Employing similar procedures alloys are prepared having the compositions and properties set forth in Table III.

TABLE III

| | COMPOSITION (in weight percent) | | | |
|---|---|---|---|---|
| | Alloy A | Alloy B | Alloy C | Alloy D |
| Ni | 71.3 | 71.3 | 71.3 | 71.3 |
| Cr | 19.1 | 19.1 | 19.1 | 19.1 |
| Si | 4.0 | 4.1 | 4.6 | 5.1 |
| Mo | 4.1 | 4.1 | 3.7 | 3.5 |
| B | 1.5 | 1.4 | 1.3 | 1.0 |
| Ultimate Tensile Strength (p.s.i) | 112,800 | 128,000 | 135,670 | 146,120 |
| Percent Elongation | 1.0 | 1.25 | 1.45 | 1.8 |
| Hardness ($R_c$) | 33 | 31 | 28 | 26 |

Samples of the alloy are tested for cutting, grinding and polishing properties as follows: (a) cutting, on a high speed lathe with a Dedco cutting wheel (carborundum wheel manufactured by Dental Development & Manufacturing Corp., Brooklyn, New York); (b) grinding with Shofu Dura Green stone (silicate, product of Shofu Dental Corp., Menlo Park, California) followed by Shofu Dura White Stone (aluminum oxide, product of Shofu Dental Corp, Menlo Park, California); (c) Polishing sequentially with (i) Shofa Dura White Stone, (ii) Dedco light glaze wheel with 25 μm aluminum oxide powder, (iii) 1.5 inch felt wheels with 9.5 μm aluminum oxide and (iv) felt wheels with diamond paste.

The foregoing properties which when applied to gold alloys would be described as Easy, may be characterized as Moderate for Alloys C and D and Hard for Alloys A and B, the latter requiring diamond paste for achieving a polish.

Alloy B when tested for corrosion resistance as described in Example 3, is found to have a weight loss of 0.111 mg/cm$^2$ per day in 0.05% hydrochloric acid, of 0.0239 mg/cm per day in 1.0% lactic acid and of 0.0080 mg/cm$^2$ per day in 1.0% aqueous sodium chloride. Alloy B when tested for oxidation resistance as described in Example 3, is found to have a weight gain of $0.4765 \times 10^{-2}$ mg/cm$^2$ -min.

All alloys are found to have thermal expansion comparable to gold alloys.

EXAMPLE 5

Into a crucible is added in order: (1) 47.5 pounds of nickel shot; (2) 2.8 pounds of boron blocks, 8.2 pounds of silicon blocks and 8.2 pounds of molybdenum plates; (3) 25.4 pounds of chromium plates; and (4) 47.5 pounds of nickel shot, and the crucible heated to a temperature of between about 1400° C. and 1600° C. to melt the contents, the heating carried out in an argon atmosphere to prevent oxidation. After the initial melt is obtained, 12.8 pounds of chromium and 47.6 pounds of nickel are placed in the crucible and the heating continued to 2700° F. to obtain a completely molten alloy. The melt is poured into resin shell molds for rods 5/16 inch in diameter.

The composition of the alloy is given below in weight percent. The original composition is the weight of raw material added; the final composition is the weight of elements on analysis of the alloy. The differences between the original and final composition is partly due to the fact that the final composition represents analytical data and partly to changes occuring at elevated temperatures.

| | ALLOY COMPOSITION | |
|---|---|---|
| | Initial | Final |
| Nickel | 71.3 | 69.63 |
| Chromium | 19.1 | 19.40 |
| Silicon | 4.1 | 3.87 |
| Molybdenum | 4.1 | 4.24 |
| Boron | 1.4 | 1.36 |
| Carbon | — | 0.04 |

Ingots (about 1 cm) are prepared from the rods and the ingots recast into tensile bars to determine mechanical properties which are found to be:

| | |
|---|---|
| Ultimate Tensile Strength | 115,000 p.s.i. |
| Yield Strength | 90,000 p.s.i. |

| Percent Elongation | 1.0 – 1.1% |
| --- | --- |

Some of the ingots are employed to prepare coping and the latter tested for hardness; the Rockwell C hardness is found to be 31 $R_c$.

Separate melting point determinations give the following ranges: 2150°–2265° F.; 2100°–2200° F.; and 2066°–2170° F.

In testing for porcelain to metal bonding strength, commercial CERAMCO opaque porcelain (product of CERAMCO, Inc., Long Island City, New York) is coated around a 14 gauge cast alloy rod and fired at about 1850° F. forming porcelain disks 0.055 to 0.082 inch thick. The disks are supported by dental stone and a tensile load applied at a crosshead rate of 0.05 cm/min. Stress values computed by dividing the tensile load by the measured bonding surface area show bond strengths significantly greater than 7300 p.s.i.

Portions of the alloy evaluated by a dental technician are found to be satisfactory for use as a dental alloy. The alloy is found to melt and cast well using a gas/oxygen torch with the oxygen pressure up to about 9 pounds per square inch. The alloy is found to undergo the repeated application and firing of porcelain without causing discoloration of the porcelain. Crowns cast from alloys, after removal of investment and metal buttons fit on original dies without difficulty. The alloy also shows good properties for soldering, cutting, grinding and polishing.

EXAMPLE 6

Using the process of Example 1, alloys are prepared having the compositions set forth in the following Table IV. These alloys are used for the applications indicated in the column identified "Applications". In each use of the alloy is observed to perform well when used by standard accepted dental laboratories techniques.

TABLE IV

| Alloy # | Ni | Cr | Mo | Si | Mn | B | Applications* |
| --- | --- | --- | --- | --- | --- | --- | --- |
| 1 | 70.42 | 19.01 | 4.20 | 5.49 | 0.68 | 0.20 | MCB,PCB,PLCB,I&O |
| 2 | 70.42 | 19.01 | 4.20 | 5.49 | 0.88 | — | MCB,PCB,PLCB,I&O |
| 3 | 71.65 | 19.09 | 4.22 | 4.02 | — | 1.02 | MCB,PCB,PLCB,I&O |
| 4 | 71.65 | 19.14 | 4.38 | 3.52 | — | 1.31 | MCB,PCB,PLCB |
| 5 | 71.09 | 19.14 | 4.32 | 3.90 | — | 1.55 | MCB,PCB,PLCB |
| 6 | 70.94 | 18.90 | 4.17 | 4.50 | — | 1.49 | MCB,PCB,PLCB |
| 7 | 70.59 | 18.81 | 4.15 | 4.95 | — | 1.50 | MCB,PCB,PLCB |

*MCB Metal Crowns and Bridges
PCB Porcelain Crowns and Bridges
PLCB Plastic Crowns and Bridges
I&O Inlay and Onlays The alloys of Table IV have the physical properties set forth in Table V.

TABLE V

| Alloy # | Specimen's Condition | U.T.S. (p.s.i.) | Y.S. (p.s.i.) | % Elongation (%) | Hardness ($R_B$) | Melting Point °F |
| --- | --- | --- | --- | --- | --- | --- |
| 1 (a) | as casted | 90,000 | 80,000 | 2.5 | 102 | 2250–2300 |
| (b) | 1850° F,* 5 min. | 100.000 | 55,000 | 11.0 | 94 | 2250–2300 |
| 2 | as casted | 104,000 | 74,000 | 4.3 | 97 | 2250–2300 |
| 3 | as casted | 120,700 | 78,000 | 2.76 | 103.4 | 2250–2300 |
| 4 | as casted | 113,000 | 78,000 | 1.60 | 103.5 | 2250–2300 |
| 5 (a) | as casted | 123,000 | 90,000 | 1.24 | 106.7 | 2200–2250 |
| (b) | 1800° F, 10* min. | 117,000 | 87,000 | 1.96 | 105 | 2200–2250 |
| 6 | as casted | 120,000 | 91,000 | 1.64 | 106.3 | 2200–2250 |
| 7 | as casted | 109,300 | 109,000 | 0.5 | 108.6 | 2200–2250 |

*After casting and cooled to room temperature, specimen is heated to temperature indicated for the time indicated and cooled to room temperature before making determinations.

EXAMPLE 7

A wax pattern is made for crowns in a conventional manner and placed in a suitable burn out furnace. An adequate amount of non-precious alloy of the composition described in Example 5 is placed in a heated crucible of an investing casting machine and heated to melt; it is heated with a gas/oxygen torch with about 9 pounds pressure of oxygen until the alloy melts. The ring then is placed in the cradle of a centrifugal casting machine and the molten metal cast in a conventional manner to obtain the desired casting of the non-precious metal alloy. Thereafter, employing conventional procedures, the casting is cooled, removed from the investment, trimmed and then ground first with Shofu Dura Green Stone (a silicate) and then with Shofu Dura White Stone (an aluminum oxide powder) to obtain an appropriately shaped non-precious metal alloy core.

The metal core is then sandblasted with quartz or $Al_2O_3$ abrasives in the areas to be covered with porcelain and polished to a finish in the shoulders and areas not to be covered with porcelain. The metal core is then placed in acid for about five minutes, rinsed with distilled water, ultrasonically cleaned with distilled water for about 15 minutes, then removed and dried.

Employing conventional procedures, an opaque porcelain having a chemical composition in weight percent of 55% $SiO_2$, 11.65% $Al_2O_3$, 9.6% $K_2O$, 4.75% $Na_2O$, 0.16% $ZrO_2$, 15% $SnO_2$, 0.04% $Rb_2O$, 0.26% ZnO and 3.54% $B_2O_3$, $CO_2$ and $H_2O$, is painted on the sandblasted area, then dried at elevated temperatures by placing at the door of the furnace. The dried metal core having a coating of opaque porcelain material is placed in a furnace preheated to 1200° F. and thereafter heated to 1700° F. under vacuum (26–29 inches Hg). At 1700° F., the vacuum is broken and the heating continued in air until a temperature of 1850° F. is reached to obtain the desired dental constuction comprising an appropriately contoured metal core having porcelain covering bonded to it.

The dental construction thus obtained is allowed to cool and thereafter successively painted with several layers of body or gingival porcelain having a chemical composition of 62.2% $SiO_2$, 13.4% $Al_2O_3$, 0.98% CaO, 11.3% $K_2O$, 5.37% $Na_2O$, 0.34% $ZrO_2$, 0.5% $SnO_2$, 0.06% $Rb_2O$ and 5.85% of $B_2O_3$, $CO_2$ and $H_2O$, and then with incisal porcelain of similar composition containing no tin oxide with firing after each application by heating in the temperature range of 1200° F. to 1700° F. under 26–29 inches Hg, followed by heating to 1800° F. in air, and then allowing to cool to obtain a dental construction comprising an artificial tooth. Corrections are made on the contour of the tooth as necessary, a final glaze is obtained by heating in air from 1200° to 1800° F., and then cooled. The tooth is finished and polished to obtain an aesthetically pleasing artificial tooth having a metal core with porcelain bonded thereto.

EXAMPLE 8

In a manner similar to that described in Example 7, an appropriately contoured non-precious metal alloy core is first prepared.

Thereafter, an aluminum-boron bonding agent of the co-pending application and of the composition previously described is applied by painting to the areas of the surface of the metal which is to be covered with porcelain. The bonding agent is placed in the furnace at 1200° F. and the temperature raised to 1850° F. in vacuum whereafter the core is removed from the furnace and allowed to cool. After cooling, the metal core is scrubbed with a tooth brush and water, thereafter placed in distilled water in an ultrasonic cleaner for five minutes, then removed and dried.

The metal core thus obtained is painted with opaque porcelain and fired in the manner described in Example 7 to obtain a dental construction having an appropriately contoured metal core having a porcelain covering bonded thereto. The dental construction thus obtained is painted and fired successively with body porcelain and incisal porcelain and then finished in the manner described in Example 7 to obtain an artificial tooth having a metal core with porcelain bonded thereto and having good aesthetic qualities.

What is claimed is:

1. A dental restorative construction comprising a metal core of a non-precious metal alloy contoured in a desired form and a porcelain covering bonded thereto, said metal core being an alloy consisting essentially of, on a weight basis, about 65 to 75 percent nickel, about 15 to 23.5 percent chromium, about 3.5 to 6 percent silicon, about 3 to 5 percent molybdenum, and about 0.2 to 2 percent boron, said alloy having a fusion temperature within the range of 2050° F. to 2350° F. and a coefficient of expansion in the range of from about $13.0 \times 10^{-6}$ in/in/° C. to about $13.8 \times 10^{-6}$ in/in.°C.

2. A dental restorative construction according to claim 1 wherein in said alloy, the chromium to nickel ratio is from about 0.24 to about 0.30 and wherein said alloy has a tensile strength of at least 90,000 psi.

3. A dental restorative construction according to claim 1 wherein said alloy consists essentially of on a weight basis, about 69 to 72 percent nickel, about 18 to 20 percent chromium, about 4 to 5.5 percent silicon, about 4 to 4.5 percent molybdenum and about 1 to 1.5 percent boron.

4. A dental restorative construction according to claim 3 wherein in said alloy the chromium to nickel ratio is from about 0.25 to about 0.26 and wherein said alloy has a tensile strength of at least 90,000 psi.

5. A dental restorative construction according to claim 1 wherein said alloy includes up to 1 percent manganese.

6. A dental restorative construction comprising a metal core of non-precious metal alloy contoured in a desired form and a porcelain covering bonded thereto, said metal core being an alloy consisting essentially of, on a weight basis, about 65 to 75 percent nickel, about 15 to 23.5 percent chromium, about 3.5 to 6 percent silicon, about 3 to 5 percent molybdenum, and 1 percent manganese, said alloy having a fusion temperature within the range of 2050° F. to 2350° F. and a coefficient of expansion in the range of from about $13.0 \times 10^{-6}$ in/in/° C. to about $13.8 \times 10^{-6}$ in/in/° C.

* * * * *